United States Patent [19]

Ryan et al.

[11] Patent Number: 4,753,035

[45] Date of Patent: Jun. 28, 1988

[54] CROSSLINKED SILICONE COATINGS FOR BOTANICAL SEEDS

[75] Inventors: John W. Ryan, Midland Township, Midland County; Donnie R. Juen, Jerome Township, Midland County, both of Mich.

[73] Assignee: Dow Corning Corporation, Midland, Mich.

[21] Appl. No.: 10,608

[22] Filed: Feb. 4, 1987

[51] Int. Cl.$^4$ .............................................. A01C 1/06
[52] U.S. Cl. ................................. 47/57.6; 47/DIG. 9
[58] Field of Search ................... 47/57.6, DIG. 9, 58, 47/DIG. 11

[56] References Cited

U.S. PATENT DOCUMENTS

| | | |
|---|---|---|
| 2,923,095 | 2/1960 | Magimel-Pelonnier et al. |
| 3,156,550 | 11/1964 | Bartels . |
| 3,294,725 | 12/1966 | Findlay et al. |
| 4,172,904 | 10/1979 | Young et al. |
| 4,198,441 | 4/1980 | Young et al. |
| 4,200,664 | 4/1980 | Young et al. |
| 4,205,096 | 5/1980 | Young et al. |
| 4,212,897 | 7/1980 | Young et al. |
| 4,221,688 | 9/1980 | Johnson et al. |
| 4,244,849 | 1/1981 | Saam . |
| 4,282,207 | 8/1981 | Young et al. |
| 4,283,387 | 10/1981 | Young et al. |
| 4,370,160 | 1/1983 | Ziemelis . |
| 4,447,984 | 5/1984 | Sampson et al. ................... 47/58 |
| 4,562,663 | 1/1986 | Redenbaugh . |
| 4,583,320 | 4/1986 | Redenbaugh . |

FOREIGN PATENT DOCUMENTS 3150631 7/1983 Fed. Rep. of Germany .

Primary Examiner—Robert E. Bagwill
Attorney, Agent, or Firm—Dennis H. Rainear

[57] ABSTRACT

The present invention relates to the use of crosslinkable silicone materials to coat botanic seeds, seedlings, meristematic tissue and plant embryos for their protection and to promote germination. The crosslinkable silicone materials are coated onto the seeds, seedlings, meristematic tissues or plant embryos and crosslinked to cure them. The silicone coatings of the present invention on the surface of the seeds, seedlings, meristematic tissues or plant embryos provide antifungal protection and can be used to carry entrapped plant adjuvants to the site of germination. The crosslinked silicone coatings are permeable to water vapor and oxygen and allow sunlight to pass through to the germinating seed.

36 Claims, No Drawings

CROSSLINKED SILICONE COATINGS FOR BOTANICAL SEEDS

BACKGROUND OF THE INVENTION

Coatings are applied to commercial seeds for a number of reasons, including binding of pesticides, retardation of germination and for the controlled release of fertilizers, plant hormones, pesticides, etc. The coatings currently used are usually water soluble or water degradable polymers. However, most of these coatings have the weakness that they are not permeable to gases and that they have a low ability to control rate of release of materials contained within them. Seed coatings generally must protect the seed mechanically but be capable of transmission of moisture, visible light, oxygen, carbon dioxide and certain other materials.

Magimel-Pelonnier et al., in U.S. Pat. No. 2,923,095, issued Feb. 2, 1960, utilized organosilicic derivatives for modifying or controlling the degree of hydration of, and transpiration of water from, vegetable material of the nature of growing plants, plants removed from the ground, cuttings of plants, seeds and the like. However Magimel-Pelonnier et al. does not teach the use of crosslinked silicone polymers for the protection of the seeds or the incorporation of additives.

Several patents issued to Young et al. teach the use of organopolysiloxanes possessing hydroxyl groups or groups hydrolyzable to hydroxyl groups for the controlled release of pesticides e.g., insecticides. See U.S. Pat. Nos. 4,282,207, issued Aug. 4, 1981; 4,212,897, issued July 15, 1980; 4,205,096, issued May 27, 1980; 4,200,664, issued Apr. 29, 1980; 4,198,441, issued Apr. 15, 1980; 4,172,904, issued Oct. 30, 1979; and 4,283,387, issued Aug. 11, 1981. However, the compositions of the Young et al. patents are prepared in organic solvents and unlike the compositions of the instant invention, cannot be prepared in water because the starting materials would rapidly and uncontrollably hydrolyze without building up an elastomeric polymer. Furthermore, the Young et al. patents do not teach the crosslinking of the polyorganosiloxanes utilized in the coating methods of the instant invention. Finally, the Young et al. patents do not teach the coating of seeds, seedlings, meristematic tissue, or plant embryos.

German patent DE No. 3150631, issued July 21, 1983 to Weber et al., relates to seed dressing with a phytotoxic pesticide incorporated into a slow-release composition. Weber et al. teaches the possible use of a silicone in the composition but requires an additional organic or inorganic binder such as methyl cellulose, polyvinyl acetate, a polyacrylate, a ureaformaldehyde resin, perlite, or vermiculite. Such additional binders are not necessary in the crosslinked silicone seed coatings of the instant invention. Weber et al. does not teach the use of crosslinked silicone polymers as the binder.

In U.S. Pat. No. 3,156,550, issued Nov. 10, 1964, to Bartels, there is taught the use of two adherent layers applied to seeds for protection. However no use of polydimethylsiloxane polymers is indicated.

U.S. Pat. No. 4,370,160, issued Jan. 25, 1983, to Ziemelis, teaches that a broad range of materials can be entrapped in cured microcapsules or microparticles of polydimethylsiloxane. While Ziemelis mentions insecticides as one of the possible materials which may be encapsulated within curable polydimethylsiloxane, no mention is made therein of seeds, seedlings, meristematic tissue or plant embryos Redenbaugh, in U.S. Pat. No. 4,562,663, issued Jan. 7, 1986, and in U.S. Pat. No. 4,583,320, issued Apr. 22, 1986, describes the use of various materials to encapsulate meristematic tissue, plant embryos, and seeds, Silicones are not mentioned.

There is a need for artificial seeds in which plant embryos, nutrients, plant hormones, and fertilizers are encapsulated, free of disease, in a coating able to provide sufficient sunlight and water vapor transmission to facilitate germination. In sugar cane, for example, there are ordinarily microorganisms present in the plants and they consume some of the plant's nutrients, reducing the amount of sucrose produced by the cane. Therefore, sugar cane growers grow a callus of cane cells in the presence of antibiotics. The cane that results when the callus cells are caused to differentiate is then free of microorganisms. However it has not been possible to make an artificial seed from these plant embryos. Rather, the embryos are propagated in a greenhouse atmosphere until fully developed cane is produced. The stalks are then cut and planted in a field. When the crop is mature, the cane stalks are cut and taken to the customer's fields and planted in rows. This process is labor intensive and suffers from the fact that cane, once cut, is subject to rapid deterioration due to desiccation and attack by airborne microorganisms.

Thus, an object of this invention is to provide a technique whereby cultivated plant tissue or seeds or seedlings or plant embryos may be insulated from harmful conditions.

SUMMARY OF THE INVENTION

The present invention relates to the use of crosslinkable silicone materials to coat botanic seeds, seedlings, meristematic tissue or plant embryos. The crosslinkable silicone materials are then crosslinked to produce cured silicone coatings on the seeds, seedlings, meristematic tissue or plant embryos. The cured silicone coatings protect the seeds, seedlings, meristematic tissue, and plant embryos from mechanical wear and other environmental stresses. The cured silicone coatings are permeable to oxygen, visible light, water vapor, and carbon dioxide and thereby promote germination. Additionally, the coatings can incorporate desirable adjuvants including, but not limited to, plant hormones, fertilizers, pesticides, nutrients, and herbicides.

DETAILED DESCRIPTION OF THE INVENTION

The properties of crosslinked silicones meet all of the requirements for an efficient seed coating. The principal requirements are permeability to water vapor, oxygen, carbon dioxide, and visible light. Additionally, silicones are nonphytotoxic and can be applied from water systems which can be crosslinked without the generation of organic compounds most of which can have a deleterious effect on the embryonic plant. The coatings of the instant invention require no heat to cure them. Thus, by "low temperature" cure in the instant invention is meant those silicone cure conditions which are free of supplemental or externally applied heat. By "cure" in the instant invention is meant reacting, such as crosslinking, of the silicone component or components with themselves or with other reactive components to such an extent as to produce a solid, non-flowing material. By "silicone" in the instant invention is meant any alkyl, dialkyl, aryl, diaryl, siloxane fluid, polymer or resin material.

The present invention relates to a method for protecting and promoting germination of botanic seeds, seedlings, meristematic tissue and plant embryos, which method comprises coating the surface of said seeds, seedlings, meristematic tissue and plant embryos with a crosslinkable silicone material, and crosslinking the silicone material on the surface of the seeds to produce a cured silicone coating on said seeds, seedlings, meristematic tissue or plant embryos, One object of the present invention is a method for obtaining botanic seeds, seedlings, meristematic tissue and plant embryos coated with a cured silicone coating, the method comprising (I) coating said seeds, seedlings, meristematic tissue, or plant embryos with a crosslinkable silicone material, and (II) effecting a cure of the silicone material at low temperature to produce a cured silicone coating thereon, thereby obtaining seeds, seedlings, meristematic tissue or plant embryos with a cured silicone coating thereon.

Many crosslinkable silicone systems are serviceable under the present invention to coat seeds, seedlings, meristematic tissue or plant embryos. Further, different seeds or plant embryos require different processes to coat them. For example, the outer natural coating of some seeds, such as, beans, is continuous, waxy, and hydrophobic. Other seeds, such as corn, are only partially wax covered and certain artificial seeds are completely hydrophilic. The present invention provides methods for coating the various natural seed surfaces.

The instant invention utilizes and incorporates by reference the silicone water based emulsion or latex polymerization technology of Findlay et al., U.S. Pat. No. 3,294,725, issued Dec. 27, 1966; the silicone water based emulsion or latex polymerization of Johnson, et al., U.S. Pat. No. 4,221,688, issued Sept. 9, 1980; the silicone water based emulsion technology of Saam, U.S. Pat. No.4,244,849, issued Jan. 13, 1981; the ultraviolet radiation curable silicone coating technology of Ziemelis, U.S. Pat. No. 4,370,160, issued Jan. 25, 1983; the Michael addition curable silicone coating technology described and claimed in the pending application Ser. No. 926,762, filed Nov. 4, 1986, in the names of P. Lo and M. Ziemelis, and titled "Curable Organopolysiloxane Composition"; and the process for preparing silicone microparticles cured by a Michael addition reaction described and claimed in the pending application Ser. No. 926,763, filed Nov. 4, 1986in the names of P. Lo and M. Ziemelis, titled "The Process For Preparing Silicone Microparticles Cured By A Michael Addition Reaction".

One of the crosslinking technologies within the scope of the present invention is the emulsion polymerization or copolymerization of silicone water based latices or emulsions, as set forth, supra, in Johnson et al., Saam, and Findlay et al. A preferred embodiment of the present invention is a water based silicone system because of the ease of dilution and the biocompatibility. A more preferred embodiment of the present invention combines the water based crosslinkable silicone technology with ambient curing conditions. The low cure temperature is important both economically and in the prevention of dehydration and destruction of the seeds, seedlings, meristematic tissue or plant embryo. A preferred silicone for the water based crosslinkable silicone seed coatings of the present invention is a hydroxy functional dimethyl siloxane polymer which is crosslinkable by various chemical methods described herein. By "hydroxy functional " in the instant invention is meant those branched or linear silicone fluid or polymeric materials possessing at least two hydroxyl groups.

Emulsion polymerization methods for making emulsions of polymers involve starting with low viscosity polymer precursors, i.e., monomers, or reactive oligomers, which are immiscible in water; a surfactant to stabilize the polymer precursor droplet in water; colloidal silica; and, depending on the polymer selected, an optional water soluble polymerization catalyst. These components are added to water, the mixture is stirred and polymerization is allowed to advance until the reaction is complete or the desired degree of polymerization is reached and a standard emulsion of the polymer is formed. If the emulsion comprises a silicone polymer which is already crosslinked, no crosslinking catalyst is needed in the emulsion and the cured silicone seed coatings of the instant invention are obtained by the removal of the water by, for example, evaporation The silicone utilized in the emulsion polymerization coating techniques of the instant invention can be a polydiorganosiloxane which imparts the character of an elastic substance to the resulting seed coating obtained by the removal of the water from the emulsion.

One silicone system within the scope of the present invention for coating seeds is based on an aqueous emulsion of a crosslinkable silicone polymer, ethyl orthosilicate and colloidal silica. An advantage of this silicone system is the ease of controlling the rubbery nature of the coating by varying the amount of colloidal silica added to the emulsion polymer. The crosslinkable silicone polymer must contain at least two silicon-bonded hydroxyl groups per molecule and there is no specific restriction on the position of hydroxyl group substitution. Aside from the silicon-bonded hydroxyl groups, the organic groups can be either monovalent hydrocarbon radicals e.g., alkyl radicals such as methyl, ethyl, propyl, and butyl; alkenyl radicals such as vinyl and allyl; aryl radicals such as phenyl; aralkyl radicals such as benzyl; alkaryl radicals such as styryl and tolyl; cycloalkyl radicals such as cyclohexyl and cyclopentyl; or the above radicals in which some or all of the hydrogen atoms have been substituted by a halogen. The organic group on the silicon atom is usually methyl, vinyl, or phenyl. It is not necessary that all organic radicals be identical and generally a combination of organic radicals is present. The molecular configuration may be linear or branched. Practical examples of this polydiorganosiloxane are hydroxy group-terminated dimethylsiloxanes, methylphenylpolysiloxanes, methylvinylpolysiloxanes or copolymers of dimethylsiloxane units and methylvinylsiloxane units, etc. These polydiorganosiloxanes can be synthesized by the ring-opening polymerization of cyclic siloxanes or by the hydrolysis of linear or branched polydiorganosiloxanes which contain hydrolyzable groups such as the alkoxy radical, acyloxy radical, etc., or by the hydrolysis of one or two or more diorganohalosilanes.

Thus, one embodiment of the coating for seeds comprises an aqueous emulsion of a hydroxy functional polydimethylsiloxane, having a viscosity in the range of about 1 Centistoke to 100 Centistokes, and a commercially available surfactant used in preparing and stabilizing the emulsion. The surfactant emulsifier may be anionic, nonionic, or cationic. The solids content of the emulsions range from about 25 to 70 weight percent. Generally, Nalcoag colloidal silica is added to the emulsion to make the final composition for application to the seeds, seedlings, meristematic tissue, or plant embryos. Nalcoag is a registered trademark of Nalco Chemical Company, Naperville, Illinois, where the colloidal silicas bearing the same designation are commercially available. The seeds are mixed with the emulsion and the polydimethylsiloxane is cured by allowing sufficient crosslinking reactions to occur to produce a stable, nontacky, solid silicone polymer coating on the seeds upon removal of the aqueous components of the emulsion.

A preferred embodiment of the silicone water based emulsion seed coating formulation comprises 100 parts by weight of a water based curable silicone emulsion polymer and 20 parts by weight of the colloidal silica.

The silicone water based crosslinkable emulsion seed coating formulations of the instant invention produce a crosslinked silicone coating on the seeds upon evaporation of the water. The modulus of the coating is a function of the amount of colloidal silica used, increasing with increasing silica content. This silicone coating system is well suited for the incorporation of water soluble materials in the coating. Urea, a fertilizer, for example, has been so incorporated by the present invention. Additionally, the coatings can incorporate desirable adjuvants including, but not limited to, plant hormones, fertilizers, pesticides, nutrients, and herbicides. By "adjuvant" in the present invention is meant plant hormones, fertilizers, pesticides, nutrients. herbicides as well as color additives or tracers used for identification or to warn of a poisonous character of other additives, among other materials. It has been recognized that plant establishment, growth and development may be enhanced by addition of adjuvants to the soil, to the rhizosphere of the plant, and to the surface of the plant, Adjuvants which have been found to be useful for encapsulation with meristematic tissue and also with seeds include, but are not limited to, those listed in columns 7, 8 and 9 of U.S. Pat. No. 4,583,320, issued to Redenbaugh on Apr. 22, 1986, said listed adjuvants being herein incorporated by reference as serviceable when entrapped in the crosslinkable silicone formulations of the instant invention.

A further embodiment of the present invention is a method wherein the crosslinking of the silicone material to produce the silicone coating on the seeds, seedlings, meristematic tissue or plant embryos comprises (A) coating the surface of seeds, seedlings, meristematic tissue or plant embryos with an aqueous emulsion of a curable polyorganosiloxane having sufficient solids content such that an essentially coutinuous film of polyorganosiloxane is formed over the surface of the seeds, seedlings, meristematic tissue or plant embryos after removal of the aqueous components of the emulsion; (B) substantially removing the aqueous components of the emulsion by drying the emulsion to form a stable, durable coating on the seeds, seedlings, meristematic tissue or plant embryos; (C) curing the resulting coating to form an essentially continuous coating of cured polyorganosiloxane on the seeds, seedlings, meristematic tissue or plant embryos.

Another embodiment of the present invention is a method of coating and planting seeds wherein the seeds, seedlings, meristematic tissue or plant embryos are mixed with a silicone water based polymer emulsion, wherein the silicone is crosslinkable upon evaporation of the water. The silicone water based polymer emulsion, water and the seeds, seedlings, meristematic tissue or plant embryos form a slurry which can be sprayed on the field by the farmer. The spraying can be widespread, or in continuous parallel rows or in discontinuous rows, i.e., spot spraying. After the slurry is sprayed on the cultivated crop field, the water will evaporate inducing crosslinking of the crosslinkable silicone polymer material which serves to protect and anchor the seeds, seedlings, meristematic tissue or plant embryos to the soil. Adjuvants can also be incorporated into the sprayable silicone water based polymer emulsion so as to further enhance germination. Thus, another embodiment of the present invention is a composition comprising a dispersion of seeds, seedlings, meristematic tissue, or plant embryos in a curable silicone water based polymer material, wherein said curable silicone water based polymer in the dispersion is crosslinkable upon the evaporation of the water. The dispersion can be deposited, with or without dilution with water, onto agricultural soil.

The cured silicone formulations of the instant invention have demonstrated anti-fungal activity in the protection of coated seeds. Additionally, seeds which had natural fungi already on them were found not to rot when planted in moist soil, but rather, when coated by the processes of the instant invention, germinated without evidence of fungal growth. The applicants believe, but do not wish to be held to the theory, that the observed effect of the silicone coating in promoting germination and retarding fungal growth is caused by the silicone coating being a physical and/or a chemical barrier preventing or delaying the invasion of the seed by the fungi resident in agricultural soils. Thus, another advantage of the coating method of the present invention is the preservative property of the seed coatings produced. Another embodiment of the curable silicone coatings of the present invention for the coating of seeds, seedlings, meristematic tissue and plant embryos is the coating produced by the Michael addition reaction utilizing the addition of an amine to an activated carbon-carbon double bond. Thus, in the presence of seeds, a silicone polymer endblocked with an organic radical bearing two acrylate ester units, and having a viscosity of about 100 Centistokes, was mixed with an equivalent amount (i.e., one nitrogen atom per olefin group) of silicone fluid polymer of 350 Centistokes viscosity and having 5% of the siloxane units bearing amino-functional groups. These materials reacted to produce a soft rubbery coating on the seeds. Harder coatings were obtained by adding 10% by weight of an amino silicone fluid polymer having 30% of its siloxane units bearing diamine functionality.

Thus another embodiment of the present invention is a method wherein the crosslinking of the silicone material to produce the silicone coating on the seeds, seedlings, meristematic tissue or plant embryos comprises (A) preparing a dispersion of seeds, seedlings, meristematic tissue or plant embryos in a fluid continuous phase by dispersing, in the continuous phase, a liquid organopolysiloxane composition, convertible to the solid state, and said liquid organopolysiloxane composition being insoluble in the fluid continuous phase and consisting essentially of (a) an organopolysiloxane having attached thereto through silicon-carbon bonds an average of at least two X groups per molecule, wherein X is a monovalent organic moiety containing at least one -NHR radical, wherein R is selected from hydrogen or alkyl having 1 to 6 carbon atoms or aminoalkyl having 1 to 6 carbon atoms, and
(b) an organopolysiloxane having attached thereto through silicon-carbon bonds an average of at least two Z groups per molecule, wherein Z is a monovalent organic moiety containing at least one acryl-functional radical, said acryl-functional radical being selected from acryloxy, methacryloxy or acrylamide radicals, at least one of (a) and (b) having an average of more than two of said X groups and said Z groups, respectively, per molecule; and (B) curing said composition by allowing the -NHR-containing material to react with the acryl-containing material in the presence of the seeds, seedlings, meristematic tissue or plant embryos until said organopolysiloxane composition is converted to the solid state, thereby forming a coating on the seeds, seedlings, meristematic tissue or plant embryos, Another method of coating seeds, seedlings, meristematic tissue, and plant embryos by the instant invention is the use of ultraviolet radiation curable silicone coating technology, This technology utilizes two or more fluids, one of which contains thiol groups and another of which bears aliphatic unsaturation. The fluids are mixed with the seeds and then the mixture is added to a stirred, water-filled reactor. Irradiation of the stirring slurry by ultraviolet light for 8 to 15 minutes produces cured silicone coatings on the seeds. Water insoluble materials can be included in the coatings for later controlled release after the seed has germinated.

Thus, another embodiment of the present invention is a method wherein the crosslinking of the silicone material to produce the silicone coating on the seeds, seedlings, meristematic tissue or plant embryos comprises (A) preparing a dispersion of seeds, seedlings, meristematic tissue or plant embryos in a fluid continuous phase by dispersing, in the continuous phase, a liquid organopolysiloxane composition, convertible by ultraviolet radiation to the solid state, said fluid continuous phase being transparent to ultraviolet radiation and said liquid organopolysiloxane composition being insoluble in the fluid continuous phase and consisting essentially of
(a) an organopolysiloxane wherein an average of at least two of the organic radicals per molecule are siliconbonded olefinic radicals selected from the group consisting of vinyl and butenyl and
(b) a hydrogen-containing organopolysiloxane, free of aliphatic unsaturation, wherein the average molecule contains at least two hydrogen radicals selected from the group consisting of silicon-bonded hydrogen and mercaptoalkyl hydrogen, at least one of (a) and (b) having an average of more than two of said olefinic radicals and said hydrogen radicals, respectively, per molecule, and (B) exposing the dispersion of (A) in the presence of the seeds, seedlings, meristematic tissue or plant embryos to ultraviolet radiation until the liquid organopolysiloxane composition is converted to the solid state, thereby forming a coating on the seeds, seedlings, meristematic tissue or plant embryos.

The ultraviolet curable liquid organopolysiloxane composition may also contain a photosensitizing amount of a photosensitizer.

If the curing of a crosslinkable silicone coating of the present invention is interrupted before the coating is completely tack-free, a sticky silicone coated seed, seedling, meristematic tissue or plant embryo is produced which provides the advantage of improved adhesion to agricultural soil. The cured silicone coatings of the instant invention are able to imbibe water, holding the water in close proximity to the germinating seed. At the same time, the silicone coatings are able to transmit oxygen sufficient for germination. Furthermore, the silicone coatings do not readily dissolve or disintegrate in moist soils. In fact, another advantage of the coatings of the instant invention is the fact that the silicone coatings do not migrate into the ground water table as liquid organic chemicals can do and, furthermore, the crosslinked silicone materials are non-toxic to plants and animals.

The instant invention is useful for the protection of seeds during shipment, storage, and planting. The coatings and methods of the instant invention are useful in improving the germination rate of seeds, seedlings, meristematic tissue and plant embryos, and are useful in carrying to the site of germination desirable components, such as pesticides, herbicides, plant hormones, fertilizers, and fungicides. The coatings of the instant invention are non-phytotoxic, water vapor permeable, and transmit sunlight to the seed within, The coatings are also useful in retarding fungal growth on the seeds.

EXAMPLE 1

An aqueous silicone emulsion was prepared comprising about 100 parts by weight dihydroxy polydimethylsiloxane having a viscosity of about 200 Centistokes and about 4.4 parts by weight tetraethoxysilane emulsified in water using 8.7 parts by weight of a commercial surfactant. Duponol WAQE, obtained from E. I. du Pont de Nemours and Company, Wilmington. Del. Emulsification was achieved by passing the emulsion twice through a mechanical homogenizer. About 2.5 parts by weight of Dowex ion exchange resin HCR-W2-H, obtained from Dow Chemical Company, Midland, Mich. was added to the emulsion and the mixture allowed to undergo copolymerization for about 10 hours at room temperature. The emulsion was filtered to remove the ion exchange resin and neutralized to pH of approximately 7.0 with ammonium hydroxide. To three 10 gram aliquots of the emulsion were added, respectively, 0.6 grams, 2.0 grams, and 3.0 grams of Nalcoag 1115 colloidal silica obtained from Nalco Chemical Company, Naperville Ill. By this method were produced a 6%, a 20% and a 30% silica silicone latexes. Using the 20% latex as a glue, 8 inch pieces of thread were glued to three beans and three wheat seeds and allowed to air dry overnight. Using the thread to handle the seeds, one bean and one wheat seed were dunked in each of three latex solutions. Each of the three beans received eight dunkings, and each of the three wheat seeds received twelve dunkings resulting in a crosslinkable silicone coating on each. After being allowed to air dry, whereby the silicone underwent crosslinking reactions to form a crosslinked coating on the bean seeds, the coated bean and wheat seeds were planted in 20 grams of dirt in paper cups, one bean or seed per cup. The plantings were heavily watered (8–9 grams per day). Uncoated control beans and seeds were also planted. All plantings were exposed to 7½ hours of incident fluorescent light each day. After six days all of the coated seeds had germinated and leaves had emerged. No growth was observed in the cups with the uncoated seeds. After six days, the uncoated seeds were removed from the soil to reveal that the uncoated seeds had been attacked by fungi evident by white fluffy products on the seeds.

EXAMPLE 2

Using the same dipping procedure as in Example 1, five beans were coated using the emulsion containing 20% silica and five beans were coated using an acrylic latex (Rhoplex AC-64) obtained from Rohm and Haas Company, Philadelphia, Pa., and five beans were coated with a styrene-butadiene latex (BF Goodrich 1800X73). All coatings were cured by allowing them to crosslink by air drying until tack free. The coated beans, along with 5 uncoated beans, were all planted in garden soil, watered and placed under 12 hour per day fluorescent illumination. The controls (no coating) and the silicone coated beans grew very well. The acrylic coated and the styrene-butadiene coated seeds did not grow and were found to have been attacked by fungus in the soil.

EXAMPLE 3

Two soybeans were coated as in Example 2 using the emulsion containing 20% silica. The beans were planted as in Example 2 and compared to two uncoated control soybeans planted in the same soil. The coated soybeans germinated in the same manner and to the same extent as did the uncoated control soybeans.

EXAMPLE 4

To 10 grams of washed rapeseed was added a mixture of 2 grams of the 20% silica emulsion of Example 1 and 1 milliliter of an aqueous solution of urea (200 grams/liter). The seed was thoroughly wetted with this mixture and the resulting coating was crosslinked by drying in air overnight, after which the mass of seeds was found to be stuck together by a cured silicone rubber. Gentle mechanical shear separated the seeds to produce individual rapeseeds coated with a silicone rubber coating containing urea.

EXAMPLE 5

Using the procedure of Example 4, a 30% silica emulsion prepared as in Example 1. above, was mixed with the aqueous solution of urea. The resulting mass of seeds was more easily divided than was the mass in Example 4 because the coating produced herein was significantly more friable.

EXAMPLE 6

Ten grams of rapeseed (washed with distilled water), 150 milliliters of water and 3 drops of Triton ® X-100, obtained from Rohm and Haas Company. Philadelphia Pa, were placed in a beaker along with a magnetic stirring bar. This mixture was stirred while 0.5 milliliter of a polydimethylsiloxane fluid, with a viscosity of 350 Centistokes, and in which 30% of the silicon atoms bear a 2-aminoethylaminoisobutyl group, and to which was added 0.25 milliliter of a 150 Centistokes polydimethylsiloxane fluid which was end-capped with two organic radicals on each molecule, each radical bearing two acryloxy groups. The mixture was stirred gently for 1 hour at ambient temperature during which time the silicone fluids underwent sufficient Michael addition-type crosslinking reactions to produce a cured coating on the seeds. The water was then decanted and the silicone coated seeds were washed with water and dried in air at ambient temperature. After drying, the rapeseeds were observed to be coated with polydimethylsiloxane as evidenced by the high contact angle made by a water droplet.

EXAMPLE 7

Corn seeds, 20 grams, were treated in the same manner as the rapeseed of Example 6. During the stirring, the crosslinkable silicone fluids underwent sufficient Michael addition-type crosslinking reactions to produce a cured silicone coating on the seeds. After drying, the corn seeds were obeerved to be coated with polydimethylsiloxane as evidenced by the high contact angle made by a water droplet.

EXAMPLE 8

Using the method of Example 7, 0.2 grams of Dursban ®, a chlorpyrifos pesticide obtained from Dow Chemical Company. Midland, Mich., was added to the stirring mixture. After drying the coated corn seeds, the Dursban ® formulation was found to have been incorporated into the silicone coating on the corn seeds.

EXAMPLE 9

Twenty milliliters of calcium alginate spheres were coated by the same procedure as in Example 6. The coated spheres were found to have lost their hydrophilic character and could be held on the surface of water by surface tension.

EXAMPLE 10

Several samples of meristematic tissue obtained from germs of corn seeds were imbedded in jelly-like calcium alginate spheres. Twenty milliliters of the spheres of calcium algiuate coated meristematic tissue were coated by the same procedure as in Example 6. The seed germs were observed to be coated with polydimethylsiloxane as evidenced by the high contact angle made by a droplet of water.

EXAMPLE 11

A mixture was prepared consisting of 6 grams of a polydimethylsiloxane fluid with a viscosity of 1500 Centistokes, in which 2% of the silicon atoms were bonded to a cyclohexenyl-ethyl group, and 3.0 grams of a polydimethylsiloxane fluid, with a viscosity of 300, in which 8% of the silicon atoms were bonded to a 3-thiopropyl group. One gram of this mixture was mixed with 10 grams of navy beans. The beans, coated with a mixture of the fluids, were added to a quartz reactor flask equipped with an ultraviolet radiation lamp and containing about 500 grams of water. The mixture was stirred while being irradiated with ultraviolet light from the lamp. During irradiation, the thiopropyl polydimethylsiloxane and the cyclohexenyl-ethyl polydimethylsiloxane underwent sufficient crosslinking reactions to produce a cured silicone coating on the beans. The beans were then separated from the water, washed with water and air dried. The beans were observed to be coated with a uniform coating of cured polydimethylsiloxane. The coated beans germinated and grew healthy plants.

That which is claimed is;
1. A method for obtaining botanic seeds, seedlings, meristematic tissue, and plant embryos coated with a cured silicone coating, the method comprising;
   (I) coating said seeds, seedlings, meristematic tissue or plant embryos with a crosslinkable silicone material, and (II) effecting a cure of the silicone material at low temperature to produce a cured silicone coating thereon, thereby obtaining seeds, seedlings, meristematic tissue or plant embryos with a cured silicone coating thereon.

2. A method as claimed in claim 1 wherein the coating is applied by a means selected from the group consisting of spray coating, dip coating, and fluidized bed coating.

3. Coated seeds, seedlings, meristematic tissue or plant embryos produced by the method of claim 2.

4. A method as claimed in claim 2 further comprising the addition of a plant adjuvant to the crosslinkable silicone material prior to cure.

5. Coated seeds, seedlings, meristematic tissue or plant embryos produced by the method of claim 4.

6. A method as claimed in claim 1 wherein the cured silicone coating is achieved by a crosslinking technology selected from the group of silicone crosslinking technologies consisting of (A) ultraviolet irradiation of a mixture of a thiol-containing silicone material and an olefinically unsaturated silicone material; (B) Michael addition reaction of an amine-containing siloxane compound and an alpha-beta olefinically unsaturated carbonyl-containing compound; and (C) silicone water based latex emulsion polymerization.

7. Coated seeds, seedlings, meristematic tissue or plant embryos produced by the method of claim 6.

8. A method as claimed in claim 6 further comprising the addition of a plant adjuvant to the crosslinkable silicone material prior to cure.

9. Coated seeds, seedlings, meristematic tissue or plant embryos produced by the method of claim 8.

10. A method as described in claim 1, wherein the method further comprises:
   (A) coating the surface of said seeds, seedlings, meristematic tissue or plant embryos with an aqueous emulsion of a curable polyorganosiloxane having sufficient solids content such that an essentially continuous film of polyorganosiloxane is formed over the surface after removal of the aqueous components of the emulsion;
   (B) removing the aqueous components of the emulsion by drying the emulsion to form a stable, durable coating;
   (C) curing the resulting coating to form an essentially continuous coating.

11. Coated seeds, seedlings, meristematic tissue or plant embryos produced by the method of claim 10.

12. A method as claimed in claim 10 further comprising the addition of a plant adjuvant to the crosslinkable silicone material prior to cure.

13. Coated seeds, seedlings, meristematic tissue or plant embryos produced by the method of claim 12.

14. A method as described in claim 1, wherein the method further comprises:
   (A) preparing a dispersion of seeds, seedlings, meristematic tissue or plant embryos in a fluid continuous base by dispersing, in the continuous phase, a liquid organopolysiloxane composition, convertible by ultraviolet radiation to the solid state, said fluid continuous phase being transparent to ultraviolet radiation and said liquid organopolysiloxane composition being insoluble in the fluid continuous phase and consisting essentially of (a) an organopolysiloxane wherein an average of at least two of the organic radicals per molecule are silicon-bonded olefinic radicals selected from the group consisting of vinyl and butenyl and (b) a hydrogen-containing organopolysiloxane, free of aliphatic unsaturation, wherein the average molecule contains at least two hydrogen radicals selected from the group consisting of silicon-bonded hydrogen and mercaptoalkyl hydrogen, at least one of (a) and (b) having an average of more than two of said olefinic radicals and said hydrogen radicals, respectively, per molecule, and
   (B) exposing the dispersion of (A) in the presence of the seeds, seedlings, meristematic tissue or plant embryos to ultraviolet radiation until the liquid organopolysiloxane composition is converted to the solid state, thereby forming a coating on the seeds, seedlings, meristematic tissue or plant embryos.

15. Coated seeds, seedlings, meristematic tissue or plant embryos produced by the method of claim 14.

16. A method according to claim 14 wherein the liquid organopolysiloxane composition, convertible by ultraviolet radiation to the solid state, further contains a photosensitizing amount of a photosensitizer.

17. Coated seeds, seedlings, meristematic tissue or plant embryos produced by the method of claim 16.

18. A method as claimed in claim 16 further comprising the addition of a plant adjuvant to the crosslinkable silicone material prior to cure.

19. Coated seeds, seedlings, meristematic tissue or plant embryos produced by the method of claim 18.

20. A method as claimed in claim 14 further comprising the addition of a plant adjuvant to the crosslinkable silicone material prior to cure.

21. Coated seeds, seedlings, meristematic tissue or plant embryos produced by the method of claim 20.

22. A method as described in claim 1 wherein the method further comprises:
   (A) preparing a dispersion of seeds seedlings meristematic tissue or plant embryos in a fluid continuous phase by dispersing in the continuous phase, a liquid organopolysiloxane composition convertible to the solid state and said liquid organopolysiloxane composition being insoluble in the fluid continuous phase and consisting essentially of
   (a) an organopolysiloxane having attached thereto through silicon-carbon bonds an average of at least two X groups per molecule wherein X is a monovalent organic moiety containing at least one -NHR radical, wherein R is selected from hydrogen or alkyl having 1 to 6 carbon atoms or aminoalkyl having 1 to 6 carbon atoms, and
   (b) an organopolysiloxane having attached thereto through silicon-carbon bonds an average of at least two Z groups per molecule, wherein Z is a monovalent organic moiety containing at least one acryl-functional radical, said acryl-functional radical being selected from acryloxy, methacryloxy or acrylamide radicals, at least one of (a) and (b) having an average of more than two of said X groups and said Z groups, respectively, per molecule; and
   (B) curing said composition by allowing the -NHR-containing material to react with the acryl-containing material in the presence of the seeds, seedlings, meristematic tissue or plant embryos until said organopolysiloxane composition is converted to the solid state, thereby forming a coating on the seeds, seedlings, meristematic tissue or plant embryos.

23. Coated seeds, seedlings, meristematic tissue or plant embryos produced by the method of claim 22.

24. A method as claimed in claim 22 further comprising the addition of a plant adjuvant to the crosslinkable silicone material prior to cure.

25. Coated seeds, seedlings, meristematic tissue or plant embryos produced by the method of claim 24.

26. Coated seeds, seedlings, meristematic tissue or plant embryos produced by the method of claim 1.

27. A method as claimed in claim 1 further comprising the addition of a plant adjuvant to the crosslinkable silicone material prior to cure.

28. Coated seeds, seedlings, meristematic tissue or plant embryos produced by the method of claim 27.

29. A method which comprises:
(A) mixing seeds, seedlings, meristematic tissue, or plant embryos with a silicone water based polymer emulsion to form a dispersion, wherein the silicone water based polymer emulsion in the dispersion is crosslinkable upon the evaporation of the water;
(B) applying said dispersion to soil;
(C) crosslinking the silicone water based polymer by allowing the water to evaporate, whereby a cured silicone coating is produced which is in contact with the soil.

30. Coated seeds, seedlings, meristematic tissue or plant embryos produced by the method of claim 29.

31. A method as claimed in claim 29 further comprising the addition of a plant adjuvant to the crosslinkable silicone material prior to cure.

32. Coated seeds, seedlings, meristematic tissue or plant embryos produced by the method of claim 31.

33. A dispersion comprising: (A) a botanical material selected from the group consisting of seeds, seedlings, meristematic tissue and plant embryos; and (B) a crosslinkable silicone material.

34. A dispersion as claimed in claim 33 further comprising water.

35. A method of retarding fungal growth on seeds, seedlings. meristematic tissue, and plant embryos comprising; (I) coating said seeds, seedlings, meristematic tissue and plant embryos with a crosslinkable silicone material, and (II) crosslinking the silicone material on the surface of the seeds to produce a cured silicone coating on said seeds, seedlings. meristematic tissue and plant embryos.

36. A method for adhering seeds, seedlings, meristematic tissue and plant embryos to soil which comprises:
(I) coating said seeds, seedlings, meristematic tissue and plant embryos with a crosslinkable silicone material;
(II) partially crosslinking the silicone material on the surface of the seeds to produce a tacky, partially cured silicone coating on said seeds, seedlings, meristematic tissue and plant embryos;
(III) applying said silicone coated seeds, seedlings, meristematic tissue and plant embryos to soil, whereby said seeds, seedlings, meristematic tissue and plant embryos, coated with said tacky, partially cured silicone coating, adhere to the soil.

* * * * *